United States Patent
Mohan et al.

(10) Patent No.: US 11,110,078 B2
(45) Date of Patent: Sep. 7, 2021

(54) COMPOSITION AND METHOD FOR TREATMENT OF DISEASES ASSOCIATED WITH CENTRAL NERVOUS SYSTEM INFLAMMATION

(71) Applicant: AMRITA VISHWA VIDYAPEETHAM, Kochi (IN)

(72) Inventors: Gopi C Mohan, Kochi (IN); Krishnakumar N Menon, Kochi (IN); Jane Jose, Kochi (IN)

(73) Assignee: AMRITA VISHWA VIDYAPEETHAM, Kochi (IN)

(*) Notice: Subject to any disclaimer, the term of this patent is extended or adjusted under 35 U.S.C. 154(b) by 0 days.

(21) Appl. No.: 16/363,977

(22) Filed: Mar. 25, 2019

(65) Prior Publication Data

US 2019/0298695 A1 Oct. 3, 2019

(51) Int. Cl.
*A61K 31/415* (2006.01)
*A61K 31/416* (2006.01)

(52) U.S. Cl.
CPC .................................. *A61K 31/416* (2013.01)

(58) Field of Classification Search
CPC .................................................... A61K 31/416
See application file for complete search history.

(56) References Cited

U.S. PATENT DOCUMENTS

| | | | |
|---|---|---|---|
| 7,199,147 B2 * | 4/2007 | Imazaki | .................. A61P 15/08 514/394 |
| 8,263,597 B2 | 9/2012 | Kuzmich et al. | |
| 9,725,450 B2 | 8/2017 | Clareen et al. | |
| 2005/0009876 A1 | 1/2005 | Bhagwat et al. | |
| 2007/0244140 A1 | 10/2007 | Hu et al. | |
| 2010/0292231 A1 | 11/2010 | Ajami et al. | |
| 2011/0136148 A1 | 6/2011 | Alper | |

FOREIGN PATENT DOCUMENTS

WO 2010065776 A2 6/2010

OTHER PUBLICATIONS

Gura et al., Science, 1997, 278:1041-1042.*
Johson, British Journal of Cancer, 2001, 84:1424-1431.*
Yu et al., Journal of Neuroscience Research, vol. 88, Issue 8, 2010, pp. 1-21.*

* cited by examiner

*Primary Examiner* — Shobha Kantamneni
(74) *Attorney, Agent, or Firm* — Convergence Intellectual Property Law P.C.; Jonathan Garfinkel

(57) ABSTRACT

The invention discloses compositions, methods and kits for use in treatment of diseases associated with CNS inflammation such as multiple sclerosis. The composition includes therapeutically effective amount of (1-H indazole-4yl-) methanol. Further, a method of inhibiting glial maturation factor beta (GMF-β) phosphorylation activity in cells is disclosed. The method of treating subjects includes administering a therapeutic effective amount of the composition. The administered composition suppresses the activity of the overexpressed GMF-β either by binding or blocking its phosphorylating sites and ameliorating the inflammatory condition. The disclosed compositions, methods and kits may be used in the treatment of diseases like multiple sclerosis, Alzheimer's disease, Parkinson's disease or cancer.

4 Claims, 9 Drawing Sheets

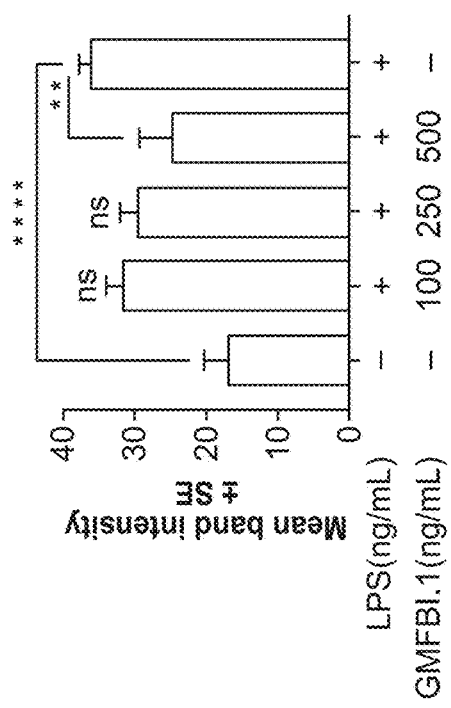
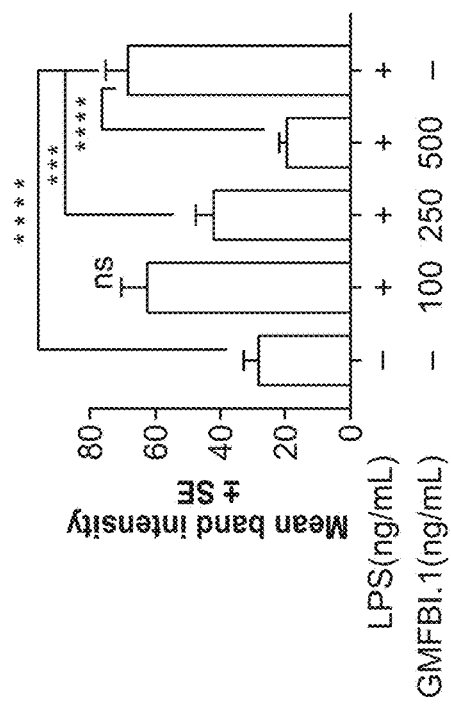
FIG. 5A
FIG. 5B
FIG. 5C
FIG. 5D

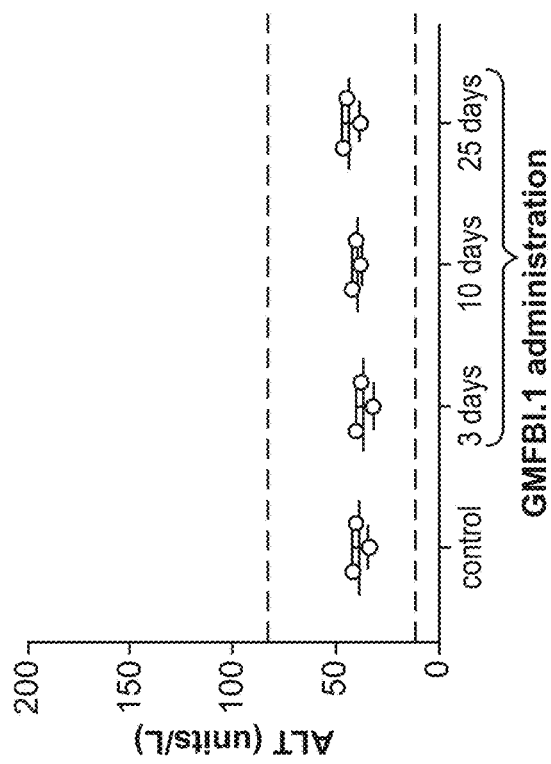
FIG. 6A
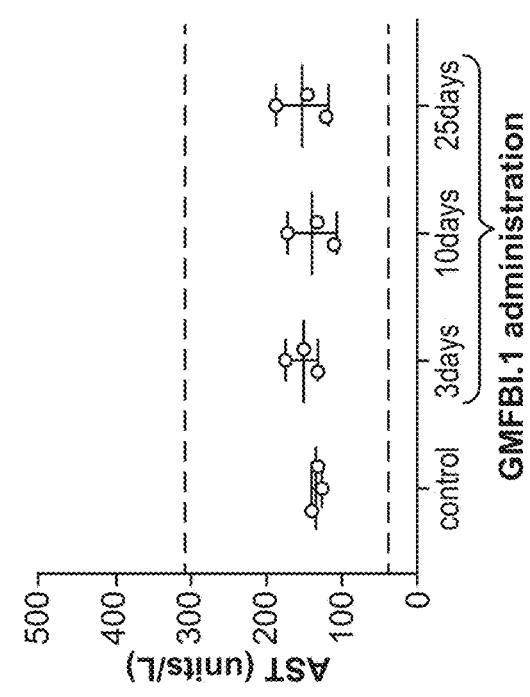
FIG. 6B
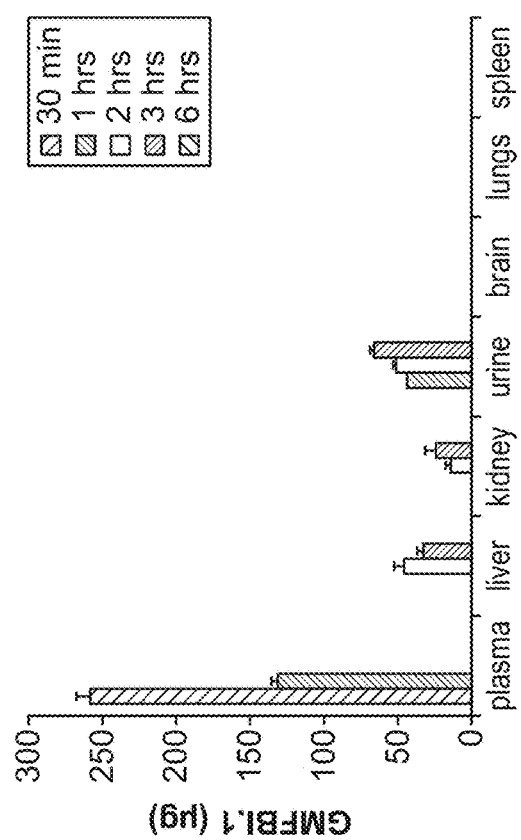
FIG. 6C
FIG. 6D

Brain

Spinal cord

COMPOSITION AND METHOD FOR TREATMENT OF DISEASES ASSOCIATED WITH CENTRAL NERVOUS SYSTEM INFLAMMATION

CROSS-REFERENCES TO RELATED APPLICATIONS

This application claims priority to Indian Provisional Patent Application No. 201841011983 entitled "A COMPOSITION AND A METHOD FOR TREATMENT OF DISEASES ASSOCIATED WITH CENTRAL NERVOUS SYSTEM INFLAMMATION" filed on Mar. 29, 2018, the full disclosure of which is incorporated herein by reference.

FIELD OF THE INVENTION

The disclosure relates generally to treatment of central nervous system (CNS) disorders and in particular to compositions, methods and kits for inhibiting autoimmune inflammatory response in CNS disorders.

BACKGROUND

Autoimmune response leading to impaired conduction of impulses as a result of neurodegeneration and demyelination results in the clinical symptoms associated with Multiple sclerosis (MS). It is a chronic autoimmune, demyelinating, neurodegenerative disorder of the central nervous system (CNS) affecting 2.5 million people globally. The pathogenesis of MS typically involves immune responses mediated by peripheral T and B-cells towards myelin proteins. Thus, severe damage to myelin proteins leads to loss of axonal integrity leading to clinical manifestations including cognitive disorders, vision problems, acute and chronic pain, improper gait and muscle weakness.

The diagnosis of MS and its severity is based on the presence of lesions in MRI of brain and spinal cord, and presence of oligoclonal bands in cerebrospinal fluid (CSF) and serum. The severity of MS is graded by standard McDonalds criteria based on clinical presentation and lesion characteristics. The disease is generally understood to be driven by Th1 and Th17 immune responses. At pathological levels, MS is characterized by infiltration of T cells from the periphery and they may clonally expand in the CNS leading to demyelination and axonal damage. Although, during normal surveillance, the immune cells do patrol the CNS, but do not produce any inflammatory response, as they are not self-reactive autoimmune cells and there is no reactive astrocyte present. However, in autoimmune disease like MS, antigens present trigger expansion of the T cells within the CNS and astrocytes become reactive and contribute an environment conducive for the T cell proliferation along with the reactive microglia.

Current therapies modulate disease differently as they target activated T cells, antigen presenting cells or prevent the egress of T cells into brain. Such treatment modalities include disease modifying therapies meant to alleviate symptoms or check the immune response by administering interferon beta 1a, interferon beta 1b, glatiramer acetate, natalizumab, fingolimod and mitoxantrone, which acts as immunosuppressants and immunomodulators. Most of these therapies available have failed to successfully cure all the symptoms of this disease with most of them having adverse side effects. Although immune targeting to suppress symptoms of MS disease has been attempted, existing therapies do not specifically target a brain-specific protein associated with proinflammatory response in the brain. Importantly, none of these drugs control molecules that modulate proinflammatory response at a fundamental level following infiltration of activated T and B lymphocytes.

GMF-β is a 141 amino acid protein predominantly expressed in brain. Many studies have shown that GMF-β is upregulated in response to immunological challenge in the animal model of MS (experimental autoimmune encephalomyelitis, EAE). Moreover, GMF-β null animals did not develop any severe clinical symptoms when challenged with the highly encephilogenetic myelin oligodendrocyte glycoprotein (MOG) antigen. The levels of infiltrating mononuclear cells into CNS from periphery was drastically reduced in the GMF-βKO condition even after challenging with MOG 35-55 peptide. Phosphorylation of GMF-β on amino acid residues Thr27, Ser53, Ser72 and Ser83 by different protein kinases is critical in its activation and regulation of inflammatory response. However, developing inhibitors against these generic kinases involved in the phosphorylation of hGMF-β is highly non-specific and could lead to adverse drug reactions.

The U.S. Pat. No. 8,263,597 B2 discloses indazole based compound as CCR1 antagonists which is described to be useful against autoimmune diseases such as rheumatoid arthritis and MS. The US patent publication US20100292231A1 describes indazole scaffolds for inflammatory disorders, demyelinating disorders, FLT3-mediated disorders, CSF-1R-mediated disorders, cancers and leukemias. The PCT publication WO2010065776 describes methods for identifying new therapeutic agents using human cell-based models. The U.S. Pat. No. 9,725,450 B2 discloses certain amino-substituted purine compounds, compositions and methods for treating or preventing certain diseases by modulating the expression of various genes. The US patent publication US 20050009876A1 describes a method for treating or preventing diseases associated with protein kinases by the use of indazole compounds. A method of treating a kinase-dependent condition, especially inflammation or cancer, by administering anilino-pyrimidine compounds is described in US patent publication US 20070244140 A1. However, none of these documents describe a specific compound for targeting a brain-specific protein associated with proinflammatory response in the brain. The US patent publication US20110136148 A1 relates to methods and kits for the immunodetection of cells or samples which express soluble or secreted GMF-β antigens. The use of the antibody in treatment and detection of cancer, Alzheimer's and dementia is described. However, the antibody is directed to the soluble form, do not cross the blood brain barrier and its effectiveness in treatment of autoimmune disease such as MS is unclear. The present disclosure describes compositions and methods for use in treatment of diseases that provides an alternative to the above therapies and overcomes some of the drawbacks of the therapies.

SUMMARY OF THE INVENTION

The present invention in its various embodiments provides for compositions, methods and kits for treatment of a central nervous system (CNS) disease or disorder. In various embodiments, included are compositions, methods and kits for binding to GMF-β and/or inhibiting GMF-β phosphorylation.

In various embodiments, a method of treating a central nervous system (CNS) disease or disorder is provided. The method includes administering a therapeutically effective amount of a compound of Formula (I):

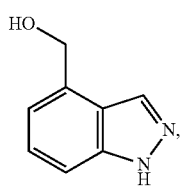

or a pharmaceutically acceptable salt thereof.

In some embodiments, the disease or disorder is selected from CNS inflammation, autoimmune disease, acute brain injury, stroke, epilepsy, multiple sclerosis, motor neuron disease, movement disorder, stroke, cerebral ischaemia, multiple sclerosis, primary progressive multiple sclerosis, relapsing remitting multiple sclerosis, demyelination, axonal damage, cancer, stroke, coronary artery disease, transient ischemic assault, hematoma, meningitis, encephalitis, ulcer, tumor, cervical spondylosis, migraine, epilepsy, dizziness, neuralgia, Alzheimer's disease, Parkinson's disease, Amyotrophic Lateral Sclerosis (ALS), Huntington's disease, and clinically isolated syndrome (CIS) associated with high proinflammatory activity. In some embodiments, the compound is administered at a daily dose of 0.1 to 100 mg/kg. In some embodiments, the compound is administered by a route selected from oral, rectal, nasal, topical, vaginal, parenteral, subcutaneous, intramuscular, intravenous, and intradermal route. In some embodiments, the compound of Formula (I) binds to GMF-β with a binding affinity in the range of −6.5 to −5.5 kcal/mol.

In various embodiments, a method of inhibiting GMF-β phosphorylation is provided. The method includes administering a therapeutically effective amount of a compound of Formula (I):

(I)

or a pharmaceutically acceptable salt thereof for treatment or prevention of a disease or disorder regulated by GMF-β.

In some embodiments, the disease is or disorder is selected from CNS inflammation, autoimmune disease, acute brain injury, stroke, epilepsy, multiple sclerosis, motor neuron disease, movement disorder, stroke, cerebral ischaemia, multiple sclerosis, primary progressive multiple sclerosis, relapsing remitting multiple sclerosis, demyelination, axonal damage, cancer, stroke, coronary artery disease, transient ischemic assault, hematoma, meningitis, encephalitis, ulcer, tumor, cervical spondylosis, migraine, epilepsy, dizziness, neuralgia, Alzheimer's disease, Parkinson's disease, Amyotrophic Lateral Sclerosis (ALS), Huntington's disease, and clinically isolated syndrome (CIS) associated with high proinflammatory activity. In some embodiments, the compound is administered at a daily dose of 0.1 to 100 mg/kg. In some embodiments, the compound is administered by a route selected from oral, rectal, nasal, topical, vaginal, parenteral, subcutaneous, intramuscular, intravenous, and intradermal. In some embodiments, the compound of Formula (I) binds to GMF-β with a binding affinity in the range of −6.5 to −5.5 kcal/mol. In some embodiments, the compound interacts with Arg24, Thr27, Ser72, Arg81, Val82, and Ser83 of GMF-β and inhibits phosphorylation of Ser83 and Thr27 of GMF-β.

In various embodiments, a composition for inhibiting GMF-β phosphorylation, comprising a compound of Formula (I):

(I)

or a pharmaceutically acceptable salt thereof for treatment or prevention of a disease or disorder regulated by GMF-β.

In some embodiments, the disease or disorder is selected from CNS inflammation, autoimmune disease, acute brain injury, stroke, epilepsy, multiple sclerosis, motor neuron disease, movement disorder, stroke, cerebral ischaemia, multiple sclerosis, primary progressive multiple sclerosis, relapsing remitting multiple sclerosis, demyelination, axonal damage, cancer, stroke, coronary artery disease, transient ischemic assault, hematoma, meningitis, encephalitis, ulcer, tumor, cervical spondylosis, migraine, epilepsy, dizziness, neuralgia, Alzheimer's disease, Parkinson's disease, Amyotrophic Lateral Sclerosis (ALS), Huntington's disease, and clinically isolated syndrome (CIS) associated with high proinflammatory activity. In some embodiments, the compound shows cell permeability of at least 500 nm/sec, oral absorption of at least 80%, blood brain barrier permeability in the range of −0.7 to −0.4. In some embodiments, the compound binds to GMF-β with a binding affinity in the range of −6.5 to −5.5 kcal/mol.

This and other aspects are disclosed herein

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 5A illustrates expression level of p38MAPK.

FIG. 5B shows mean band intensity of p38MAPK.

FIG. 5C illustrates expression level of NFκ-B.

FIG. 5D shows mean band intensity of NF-κB.

FIG. 6A shows graphically the levels of aspartate amino transferase (AST) in GMFBI.1 compound.

FIG. 6B shows graphically the levels of alanine amino transferase (ALT) in GMFBI.1 compound.

FIG. 6C shows the GMFBI.1 compound distribution in various compartments of normal healthy mice.

FIG. 6D shows the GMFBI.1 compound in EAE mice brain.

DETAILED DESCRIPTION

Figure 1B:
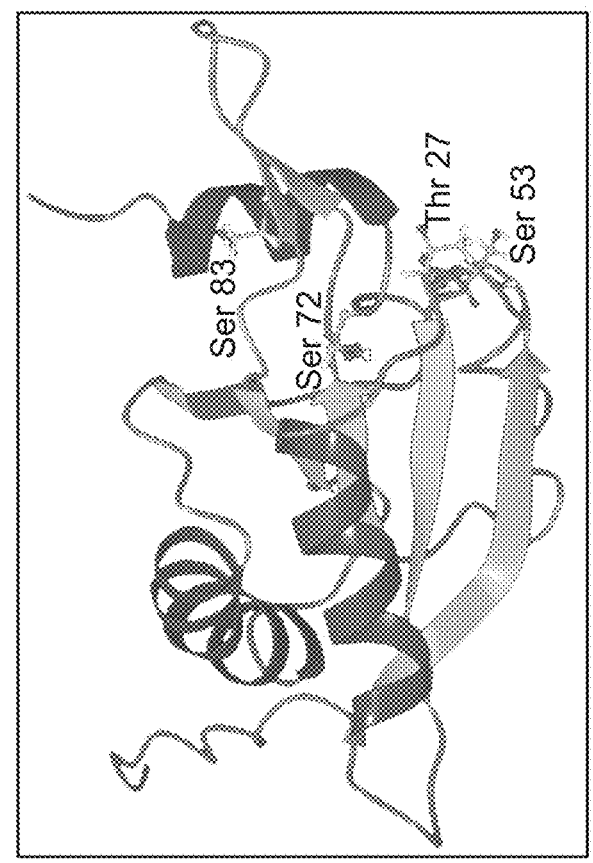
FIG. 1B illustrates active site SITE1 and SITE2 prediction of human GMF-β.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The terms "treat", "treating", and "treatment" refer to a method of alleviating or abrogating a disease and/or its attendant symptoms.

The terms "prevent", "preventing", and "prevention" refer to a method of preventing the onset of a disease and/or its attendant symptoms or barring a subject from acquiring a disease. As used herein, "prevent", "preventing", and "prevention" also include delaying the onset of a disease and/or its attendant symptoms and reducing a subject's risk of acquiring a disease.

The phrase "therapeutically effective amount" or "pharmaceutically effective amount" means a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

In various embodiments, a composition for use in treatment of a central nervous system (CNS) disease or disorder. The disease or disorder may be associated with CNS inflammation. The composition includes a therapeutically effective amount of (1-H Indazol-4-yl)-methanol denoted as GMFBI.1, and represented by Formula (I), or a pharmaceutically acceptable salt thereof.

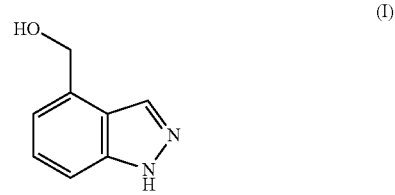 [SMILES: OCc1cccc2[nH]ncc12]

In some embodiments, the composition is used for treatment of autoimmune diseases including multiple sclerosis. In some embodiments, the composition inhibits pro-inflammatory response associated with the disease such as a brain disease in a subject. In some embodiments, the composition attenuates Th1 and Th17 mediated immune response in a subject. In some embodiments, the composition attenuates production of one or more inflammatory mediators in astrocytes and/or mast cells and/or peripheral blood mononuclear cells (PBMCs). In some embodiments, the composition attenuates Th1 and Th17 mediated immune response associated with a central nervous system disease or disorder. In some embodiments, the composition attenuates p38MAPK and/or NFκB activation in astrocytes and/or mast cells and/or peripheral blood mononuclear cells (PBMCs).

In some embodiments, a therapeutically effective amount of the composition is used for treatment of primary progressive multiple sclerosis, secondary progressive multiple sclerosis and relapsing remitting multiple sclerosis. In some embodiments, an effective amount of composition may be used to treat clinically isolated syndrome (CIS) associated with high proinflammatory activity. In some embodiments, an effective amount of the composition may be used to treat other CNS inflammations and related diseases such as autoimmune diseases, acute brain injury, stroke, epilepsy, motor neuron disease, movement disorders, stroke, cerebral ischaemia, demyelination, axonal damage, cancer, stroke, coronary artery disease, transient ischemic assault, hematoma, brain or spinal line damage, meningitis, encephalitis, ulcer, tumor, cervical spondylosis, migraine, epilepsy, dizziness, neuralgia, Alzheimer's disease, Parkinson's disease, Amyotrophic Lateral Sclerosis (ALS), Huntington's disease and clinically isolated syndrome (CIS) associated with high pro inflammatory activity.

In some embodiments, the composition includes one or more additional agents such as diluents, excipients and/or pharmaceutically acceptable carriers. In some embodiments, the compound may include its isotopically labeled form. In some embodiments, composition is conjugated with one or more additional agents such as a small molecule drug or antibody. In some embodiments, the composition is used in combination therapy with other agents for an effective therapy. The combinations may be materials or particles or other molecules either conjugated with the drug or free standing in the solution. In various embodiments, derivatives of the composition may be used to improve the absorption and retention characteristics of the composition. In accordance with another aspect of the invention there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.1 mg to 1 g, typically 1 mg to 500 mg, more preferably 5 mg to 100 mg of a compound of formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Size of the dose that accompany the compound (I) is determined by the existence, nature and extent of any adverse side-effects in a subject. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), peritoneal, vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s). In addition, compounds of the present invention can be administered using conventional drug delivery technology, for example, intra-arterial stents.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions. Pharmaceutically acceptable carrier used herein, maybe a non-toxic, inert solid, semi-solid, or liquid filler, diluent, encapsulating material, or formulations auxiliary of any type. For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like.

Lubricants used in these dosage forms include sodium oleate, sodium chloride, and the like. Disintegrators include, without limitation, starch, methyl cellulose, agar, bentonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an alginate, gelating, or polyvinyl pyrrolidone, a solution retardant such as paraffin, a resorption accelerator such as a quaternary salt and/or and absorption agent such as bentonite, kaolin, or dicalcium phosphate. The powder mixture can be granulated by wetting with a binder such as syrup, starch paste, acacia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethyl alcohol, isopropyl alcohol, ethyl carbonate, ethyl acetate, benzyl alcohol, benzyl benzoate, propylene glycol, polyethylene glycols, tetrahydrofurfuryl alcohol, ethoxylatedisostearyl alcohols, polyoxyethylene sorbitol and sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The composition may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The composition may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsiloncaprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for treatment of diseases associated with CNS inflammation, for example MS, will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the above-mentioned conditions. The composition may be administered together or separately and when administered separately this may occur simultaneously or sequentially in any order. The amounts of the compound(s) of formula (I) and the other pharmaceutically active agent(s) and the relative timings of administration will be selected in order to achieve the desired combined therapeutic effect.

In some embodiments, the composition is suitable for ameliorating the EAE clinical scores of various grades from 4, 3, 2, 1 to 1 and 0 after 30 days of administration via intraperitoneal route.

In some embodiments, the composition is non-toxic to human cells, typically human astrocytes, at concentrations of about 1 µg/ml to about 1 g/ml, typically about 0.01 to about 1 mg/ml (or 0.065-6.5 mM).

In some embodiments, the composition inhibits hGMF-β phosphorylation at concentrations of about 1 µg/ml to about 1 g/ml, typically about 0.01 to about 1 mg/ml (or 0.065-6.5 mM).

In various embodiments, a method of treatment of disease associated with CNS inflammation is provided. The method includes administering to the patient a therapeutically effective amount of the composition (1-H Indazol-4-yl)-methanol denoted as GMFBI.1, and represented by formula (I), or a pharmaceutically acceptable salt thereof.

In some embodiments, the method involves administration of the composition daily. In another embodiment, the composition is administered more than once daily. In one embodiment, the composition is administered at an amount in the range of 1 to 100 mg/kg. In select embodiments, the composition may be administered at an amount in the range of 10 to 15 mg/kg/day.

In some embodiments, administration of the composition decreases the progression of disease. In one embodiment, the composition halts the progression of disease. In another embodiment, administration of the composition increases the time of disease progression.

In various embodiments, a composition, kit and method for binding to GMF-β and/or inhibiting GMF-β phosphorylation activity in cells is provided. The method includes administering to the patient a therapeutically effective amount of the composition (1-H Indazol-4-yl)-methanol denoted as GMFBI.1, and represented by formula (I), or a pharmaceutically acceptable salt thereof. In some embodiments, the composition is administered in vitro. In some embodiments, the composition is administered in vivo. In some embodiments, the composition interacts with Ser83 and Thr27 of human GMF-β and blocks its phosphorylation mediated activity leading to inhibition of CNS inflammation. In some embodiments, the composition blocks the phosphorylating residues of GMF-β by blocking the active site pocket of the protein. In some embodiments, an effective amount of composition may block the phosphorylating sites thereby ameliorating the inflammatory condition in a subject with multiple sclerosis disease. In some embodiments, the composition suppresses the pro-inflammatory responses mediated by GMF-β including increased p38 MAPK and NF-κB activity. In some embodiments, the composition suppresses the expression levels of proinflammatory cytokines such as TNF alpha, GMCSF, IFN gamma, IL-17, and increases the expression of anti-inflammatory cytokines such as TGF beta and IL-10.

In some embodiments, the cells are neurons, glial cells, endothelial cells, fibroblasts, pericytes, macrophages, monocytes, leukocytes, plasma cells, mast cells, adipocytes, cancer cells, astrocytes, mast cells, peripheral blood mononuclear cells (PBMCs), or a combination thereof.

In some embodiments, the cell permeability is at least 500 nm/sec. In some embodiments, oral absorption is at least 80%. In some embodiments, blood brain barrier permeability in the range of −0.7 to −0.4. In some embodiments, the compound shows blood-brain barrier permeability value in the range of −0.4 to −0.6, typically about −0.511. In some embodiments, the BBB permeability of the compound is detected in EAE induced mice by intraperitoneal administration.

In some embodiments, the compound binds to GMF-β with a binding affinity in the range of −6.5 to −5.5 kcal/mol, typically −6.14 kcal/mol.

In some embodiments, the number of cellular infiltrates in brain and spinal cord for disease affected subjects is significantly decreased in subjects administered with the composition. In some embodiments, the spread of disease (cellular infiltrates) in brain and spinal cord is decreased by at least 50%, at least 60%, at least 70%, at least 80%, at least 90%, or higher.

Without being bound to any particular theory, it is suggested herein that (1H-indazol-4-yl) methanol has a particularly high specificity towards phosphorylating site residues Thr27 & Ser83 of glia maturation factor beta (GMF-beta). (1H-indazol-4-yl) methanol specifically binds to GMF-beta at the sites specified (Thr27 & Ser83) resulting in the blockage of phosphorylation of GMF-beta leading to suppression of pro-inflammatory response mediated by astrocytes and microglia. GMF-beta is involved in various functions related to inflammation including Alzheimer's, Parkinson's, Cancer, etc. The disclosed composition has application in treating these diseases. The compound may work on CNS astrocytes expressing GMF-beta in MS patients. Additionally, GMF-beta may be highly expressed in various other cell types of MS patient such as mast cells, peripheral blood mononuclear cells which may be blocked by the compound. Furthermore, certain cytokines may upregulate their expression in cells.

As defined herein, a suitable amount or a therapeutically effective amount of the compound may be assessed using techniques well known in the art such as by using animal models to obtain a concentration range and route of administration. The information obtained from these models may be used to determine the route of administration and doses in humans.

While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

EXAMPLES

Example 1: Homology Modeling of Human GMF-β Protein for Structure-Based Inhibitor A three dimensional (3D) structure of human GMF-β was developed using homology modeling technique. In order to develop this model amino acid sequence of human GMF-β was obtained in FASTA format from the NCBI protein sequence database (gi|4758442|ref| NP_004115.1). Basic local alignment search tool (BLAST) search against this query sequence was performed by choosing the protein data bank (PDB) in order to retrieve the best experimental 3D template structure for homology model development of human GMF-β protein. Murine GMF-β protein (PDB ID: 1V6F) structure was obtained as the best structure solved using NMR technique as the best hit having BLAST score of 274, E-value of 1e-94 and sequence identity of 98% respectively.

MODELLER 9v9, a computer program that models the 3D structure of proteins and their assemblies by satisfaction of spatial restrains was used for building the homology model of human GMF-β. The predicted 3D model of human GMF-β was further evaluated using PROCHECK and ERRAT programs in SAVES server, to determine the stereo chemical quality of the structure. The homology model of human GMF-β 3D structure is presented in FIG. 1A and active site residues involved in phosphorylation Thr27, Ser53, Ser72 and Ser83 are highlighted in ball and stick representation.

Figure 1A:
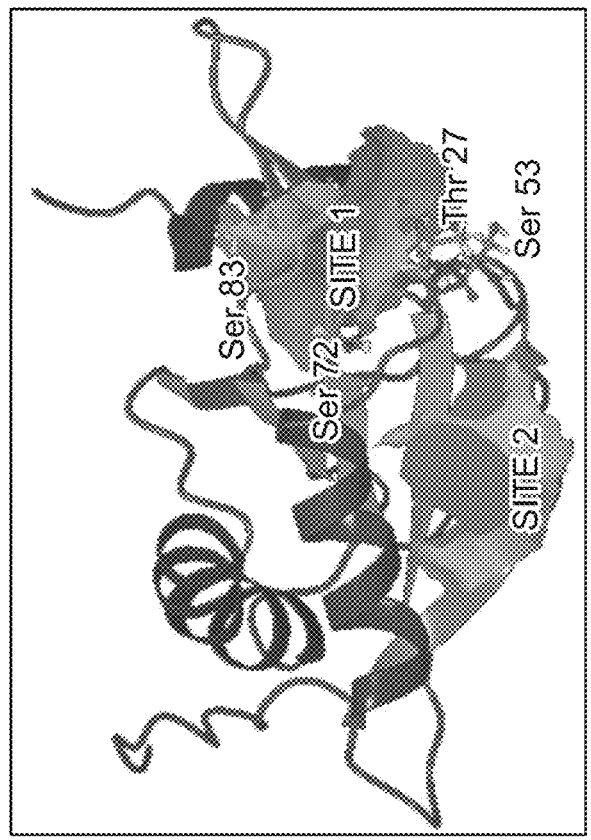
FIG. 1A illustrates homology model of human GMF-β.

Further, the active site residues involved in phosphorylation of the human GMF-β protein was predicted excellently using the SiteMap module of Schrodinger program. The best site predicted region SITE1 involve the key phosphorylating residues like Thr27, Ser72 and Ser83 of human GMF-β as shown in FIG. 1B and which in turn contribute in its downstream neurological signaling mechanisms established earlier by biochemical experiments.

Figure 2:
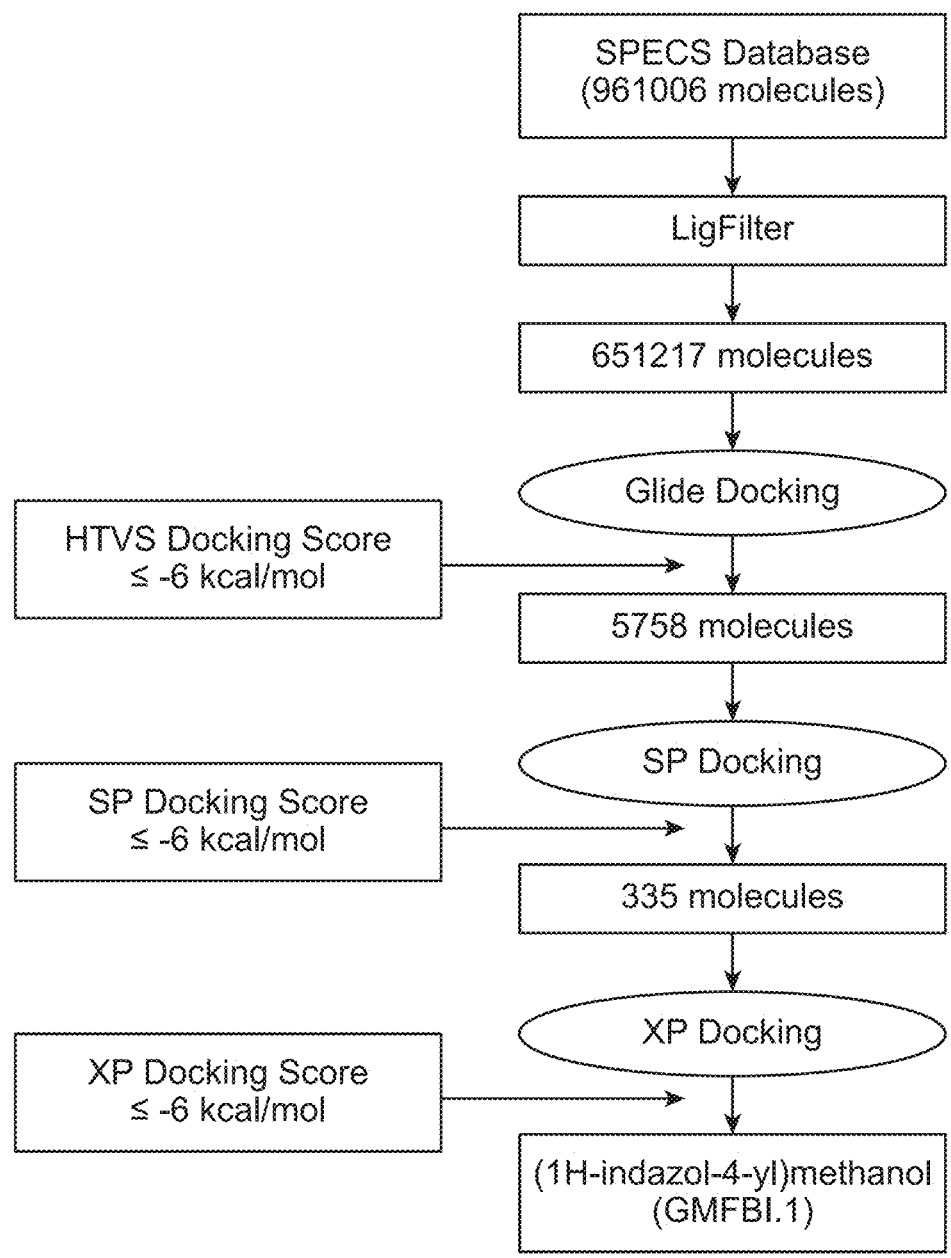
FIG. 2 illustrates the method of sequential virtual screening using SPECS database

Example 2: Sequential Virtual Screening to Identify Potent and Safe Inhibitor Inhibitor design studies were done for blocking the phosphorylation sites to suppress the downstream signaling mechanisms. An exemplary method to identify a potent and safe inhibitor (or blocker) against human GMF-β as shown in FIG. 2 involves a high-throughput sequential virtual screening (VS) technique using 961006 molecules from SPECS database. This method is used to identify best predicted small molecule against human GMF-β. Initial step of VS was Lipinski's rule of five followed by molecular docking based VS. Further, three different steps HTVS, SP and XP of glide molecular docking methodology screened (1-H indazole-4-yl) methanol, a small molecule GMFBI.1 with structure as represented in Table 1 as the best putative hit with XP docking score >−6 kcal/mol (BE). The structure, IUPAC name and properties of this molecule are given in Table 1 and the recommended range of properties of the molecule for treatment of diseases is provided in Table 2. The Caco-2 cells as illustrated in Table 1 and Table 2 are model for the gut blood barrier. The predictions are made using QikProp programs and the predictions are for non-active transport. This molecule GMFBI.1 was further subjected to ADMET studies and experimental validations (in vitro followed by in vivo) to test the efficacy of the new drug GMFBI.1 treating autoimmune disease such as multiple sclerosis (MS).

TABLE 1

Experimental results showing the properties of molecule GMFBI.1

| Ligand structure and IUPAC name | Binding affinity (kcal/mol) | Interacting residues | M.W (Da) | CNS activity | QPlog BB | PHOA | Qplog HERG | QPP Caco |
|---|---|---|---|---|---|---|---|---|
| 1H-indazol-4yl) methanol(GMFBI.1) 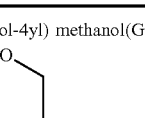 | −6.143 | Arg24, Thr27, Ser72, Arg81, Val82, Ser83 | 148.2 | −1 | −0.511 | 81.4 | −3.59 | 684.44 |

MW = Molecular weight of the molecule,
CNS = predicted CNS activity on a −2 (inactive) to +2 (active) scale,
Percent Human Oral Absorption (PHOA) = Predicted human oral absorption on 0 to 100% scale.

TABLE 2

Recommended Range of Properties of Molecule

| Parameters | Recommended range |
|---|---|
| Brain/blood barrier partition coefficient (QPlogBB) | −3.0 to 1.2 |
| Percent Human-Oral Absorption (PHOA) | >80% is high, <25% is poor |
| IC50 value for blockage of HERG K+ channels (Cardiotoxicity) (QPlogHERG) | >−5 |
| Predicted apparent Caco-2 cell permeability in nm/sec (QPPCaco). | <25 is poor, >500 is great |

Several FDA approved small molecule drugs and compounds in different clinical phase trials for the treatment of MS disease are compared for its ADMET properties with GMFBI.1 and is presented in Table 3.

TABLE 3

ADMET Prediction of Small Molecule Drugs for MS in Comparison with GMFBI.1

| Name(status/Target) | Structure | M.W (Da) | CNS activity | QPlog BB | PHOA | QPlog Herg | QPP Caco |
|---|---|---|---|---|---|---|---|
| GMFBI.1 Present study/ (EAE)(GMF-β) | 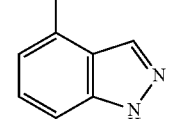 | 148.2 | −1 | −0.51 | 81.4 | −3.59 | 684.4 |
| Ind-Cl (EAE/ Estrogen receptor) | 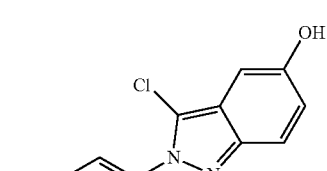 | 260.7 | −1 | −0.53 | 92.3 | −5.06 | 646.6 |
| Dimethyl Fumarate (Phase III/ Unknown immune-modulator) | 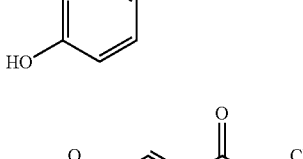 | 144.1 | 0 | −0.84 | 74.3 | −3.52 | 434.4 |
| Teriflunomide (Phase III/MS target Unknown) | 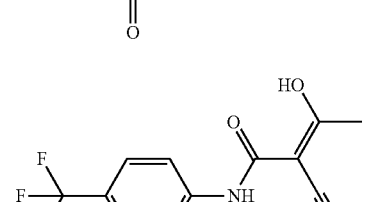 | 270.2 | 0 | −0.36 | 92.6 | −4.98 | 1153.3 |
| Fingolimod (Prescribed drug/ Sphingosine-1 receptor) | 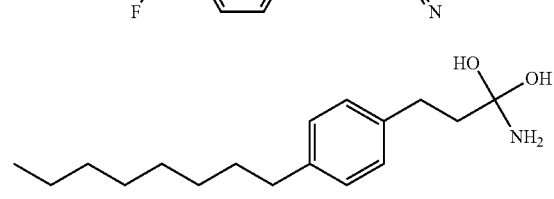 | 313.5 | −2 | −1.298 | 83.9 | −5.62 | 152.6 |
| Clemastine (antihistamine/ histamine antagonist) | 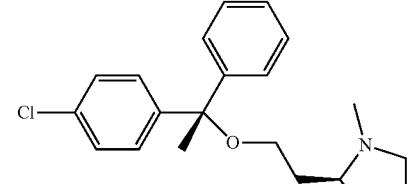 | 343.9 | 1 | −0.475 | 100 | −7.01 | 2470.6 |

TABLE 3-continued

ADMET Prediction of Small Molecule Drugs for MS in Comparison with GMFBI.1

| Name(status/Target) | Structure | M.W (Da) | CNS activity | QPlog BB | PHOA | QPlog Herg | QPP Caco |
|---|---|---|---|---|---|---|---|
| 14-dehydro ergosterol | | 394.6 | 0 | −0.209 | 100 | −4.73 | 3428.6 |
| Rivaroxaban | | 435.8 | −1 | −0.754 | 85.1 | −5.61 | 428.4 |

Figure 3B:
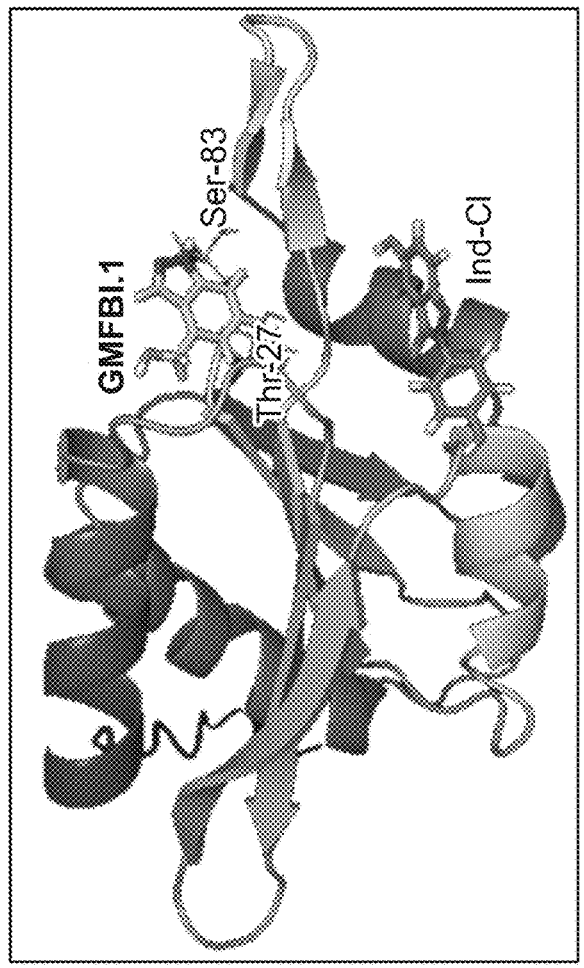
FIG. 3B shows docking of human GMF-β with Ind-Cl compound.
Figure 3A:
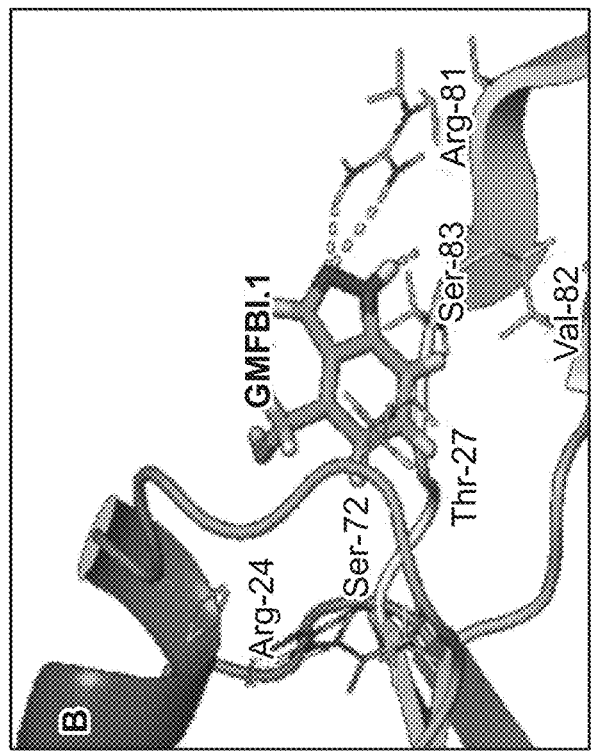
FIG. 3A shows docking of human GMF-β with GMFBI.1 compound.

Example 3: GMFBI.1 Compound Binds to the Phosphorylation Sites of Human GMF-β with High Specificity In Silico The computational study involves blocking the key phosphorylating residues of human GMF-β by other kinases, so that further downstream expression of astrocytic signaling proteins (p38 MAPK and NF-κB) would be suppressed and which would in turn prevent the proinflammatory response. The GMFBI.1 (1-H indazole-4yl methanol) compound made strong hydrogen bonding interactions and other non-bonded (van der Waals, hydrophobic) interactions towards the key residues Thr27, Arg81, Val82, Ser83 and Tyr84 of human GMF-β active site regions with high binding affinity (BE=− 6.143 kcal/mol), as shown in FIGS. 3A and 3B. The molecule showed direct hydrogen bonding interaction with different key residues within the active site area of human GMF-β.

Hydrogen bonding interactions of amino acid residues (line representation) of GMF-β with GMFBI.1 (stick) compound was represented with yellow dotted lines and the active site gorge comprising GMF-β phosphorylating residues (Thr27, Ser72 and Ser83) are marked in magenta in FIG. 3A. By comparison, several other indazole derivatives did not show effective binding at the phosphorylating residues as illustrated in FIG. 3B for indazole chloride (Ind-Cl) compound which showed non-specific binding with a binding affinity of only −3.028 kcal/mol. Therefore, binding of 1-H indazole-4yl methanol to active sites of GMF-β is highly specific for the particular derivative and blocks the phosphorylation mediated activity of GMF-β.

Example 4: In Vitro Validation of the GMFBI.1 Compound

Example 4A: Effect of GMFBI.1 Compound on Cultured Astrocyte Survival

Figure 4A:
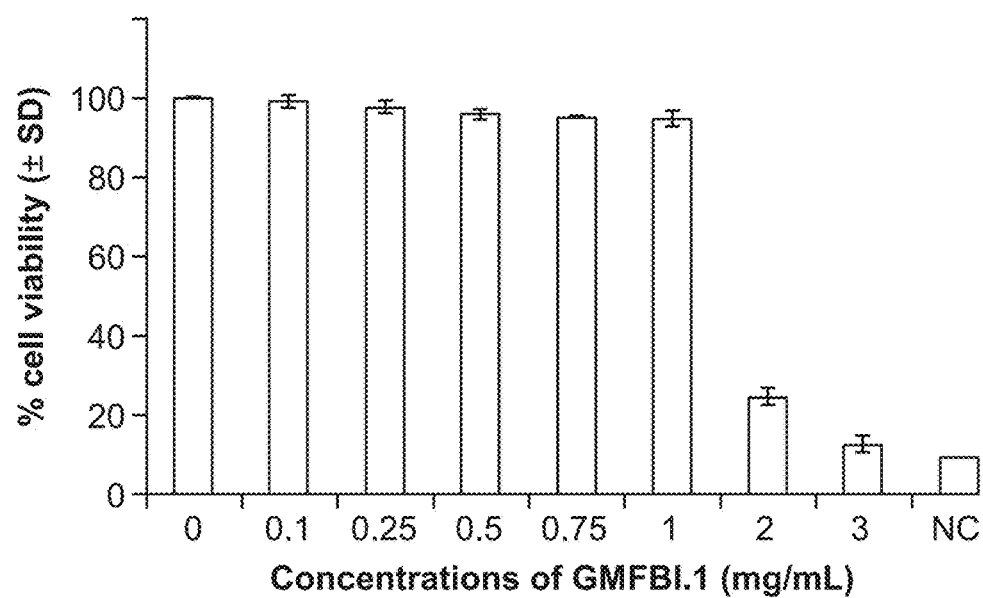
FIG. 4A shows cell viability of astrocytes incubated with increasing concentrations of GMFBI.1 compound for 48 hrs.

In order to test whether virtually screened GMFBI.1 drug like compound is toxic to the cells, different concentrations (0-3 mg/mL) of GMFBI.1 on astrocytes were tested. Test includes performing MTT cell viability assay following 48 hours of incubation with GMFBI.1. As shown in FIG. 4A, upto 1 mg/mL concentrations of the GMFBI.1 compound (inhibitor), the astrocytes remained viable. NC represents negative control with 10% Triton X-100.

Figure 4B:
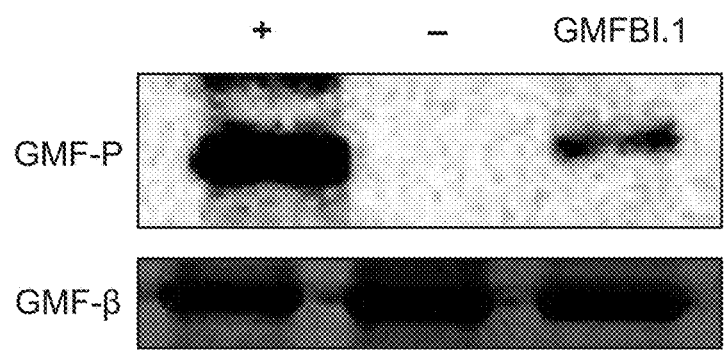
FIG. 4B illustrates difference in the levels of GMF-β expression in unstimulated (U), LPS (100 ng/mL) stimulated astrocytes.

Example 4B: GMFBI.1 Binds to the Phosphorylation Sites of GMF-β and Inhibits the Phosphorylation by PKA In Vitro With the in silico proof of concept showing high binding efficacy to GMF-β phosphorylation sites, in vitro phosphorylation studies using PKA (PKA phosphorylation results in activation of the downstream proinflammatory cascade) and purified GMF-β in presence and absence of GMFBI.1 compound is performed. As shown in FIG. 4B, upper panel represents the phosphorylation on GMF-β and lower panel represents the GMF-β levels in all the experiments. It was observed that in presence of GMFBI.1 compound, a several fold decrease in phosphorylation of GMF-β was noticed compared to the lane where no GMFBI.1 compound is added. In FIG. 4B, "+" sign indicates experiment with 1 μg/mL GMF-β and PKA, "−" indicates control reaction in the absence of PKA and "GMFBI.1" indicates phosphorylation level on GMF-β in the presence of small molecule GMFBI.1 (250 ng/mL).

Figure 4C:
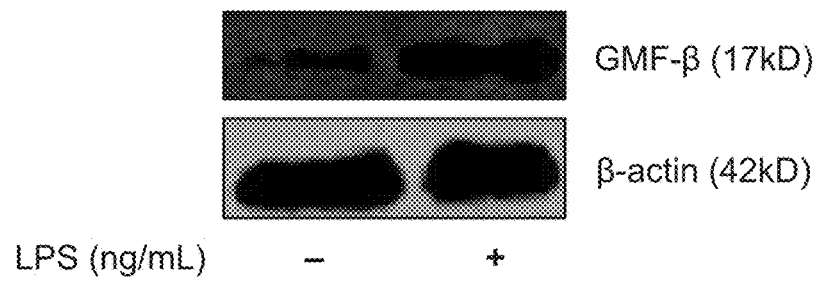
FIG. 4C shows quantitative comparison of mean band intensities of unstimulated (U) and LPS (100 ng/mL) stimulated astrocytes.

The difference in the levels of GMF-β expression in unstimulated (U) and lipopolysaccharide (LPS, 100 ng/mL) stimulated astrocytes were tested and shown in FIG. 4C. The quantitative comparison of mean band intensities of unstimulated (U) and LPS (100 ng/mL) stimulated astrocytes is determined as illustrated in FIG. 4C.

Example 4C: GMFBI.1 Compound Inhibited the Up Regulation of p38 MAP Kinase and NFκB In Vitro In order to verify the effect of GMFBI.1 compound on the pro-inflammatory cascade initiated by GMF-β over expression as seen in the brains of EAE animals, GMF-β is over expressed in cultured astrocytes by stimulating with LPS as shown in FIG. 5A and FIG. 5C. It was observed that in presence of increasing concentrations of the GMFBI.1 compound, expression was increased and at 500 ng/mL concentrations, the GMFBI.1 compound showed statistically significant suppression of p38MAPK and NFκB proteins (n=3 p≤0.05*, p≤0.01, p≤0.001*, p≤0.001****). GMFBI.1 compound reduced the expression levels of proteins downstream of GMF-β signaling in vitro.

Example 5: In Vivo Toxicity and Bio-Distribution of GMFBI.1 Compound in Animal Model In vitro efficacy of GMFBI.1 compound in down regulating the expression of both proinflammatory mediators p38MAPK and NFκB under the control of GMF-β and its non-toxic nature at lower concentrations was first evaluated. The levels of aspartate amino transferase (AST) and alanine amino transferase (ALT) were measured spectrophotometrically from serum of GMFBI.1 compound administered animals to monitor its liver function as shown in FIG. 6A and FIG. 6B respectively. No significant difference were observed in the levels of AST and ALT liver enzymes in GMFBI.1 compound administered (14 mg/kg twice daily) from saline administered controls at 3, 10 and 25 days (n=3 per group). Grey shaded region denotes the normal range of AST and ALT enzymes in mice in FIG. 6A and FIG. 6B respectively.

The GMFBI.1 compound distribution in various compartments (organs, plasma & urine) of normal healthy mice at different time intervals (30 minutes, 1, 2, 3 and 6 hours) and its distribution profile (n=3 per group), is shown in FIG. 6C. On intraperitoneal injection of GMFBI.1 300 μg to C57BL/6 mice (n=3), it was observed that at 30 mins to 1 hr, most of the GMFBI.1 compound remained in the plasma. However, by two hours, no GMFBI.1 compound could be detected in plasma. Notably, within three hours, the amount of GMFBI.1 compound detected in the liver is significantly reduced compared to 2 hrs and found majorly in urine and transiently seen in kidney. Notably by 6 hrs, no free GMFBI.1 compound in any of the organs were detected. It was observed from FIG. 6D that no GMFBI.1 compound was detected in the brains of these animals following injection at any time period analyzed. Further, again 300 μg of GMFBI.1 was injected in EAE animals and the blood brain barrier is compromised as in MS patients. The observations indicates that within 2 hrs, GMFBI.1 compound maybe detected in the brains of EAE animals and by 3 hrs, a maximum of 15 μg of the compound may be seen in the brain. However, by 6 hrs, no GMFBI.1 may be detected in the brain. Based on these observations, mice was injected twice daily with 300 μg/mice (12 mg/Kg) GMFBI.1 for 25 days. Both AST and ALT activity was measured at 3, 10 and 25 days. As shown in FIG. 6A and FIG. 6B, the activity levels of both AST and ALT remained similar to that of control despite giving injection for 25 days continuously.

Figure 7A:
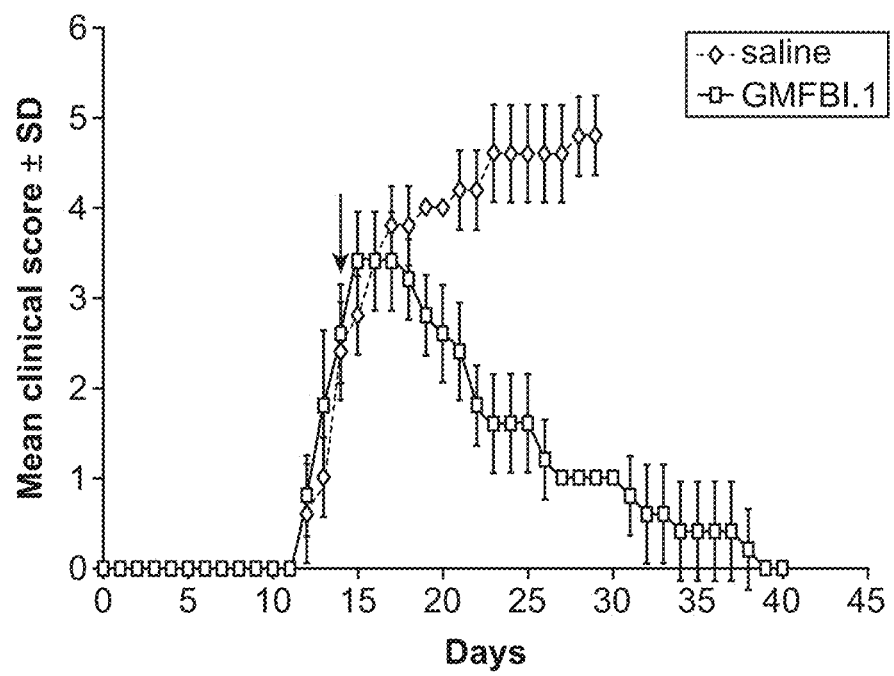
FIG. 7A shows the mean clinical score as a function of GMFBI.1.

Example 6: Reversal of EAE Following Administration of GMFBI.1 in Paralyzed EAE Animals Example 6A: GMFBI.1 Compound Treated Mice Reverted EAE Pathology Based on the observations that GMFBI.1 compound is able to cross the blood brain barrier in EAE mice and may be retained in the system for at least three hours, was able to suppress the phosphorylation on GMF-β and reduced the expression levels of p38MAPK and NFκB. Treatment was given to a group of animals with average clinical score of 3 for a period of 2 weeks. EAE induced animals were injected at clinical score 3.5 with GMFBI.1 compound 300 μg/mice (12 mg/Kg) twice daily at day 13. EAE clinical scores of C57BL/6 mice treated with GMFBI.1 compound (14 mg/kg i.p twice daily) and controls with saline (n=5 per group) is shown in FIG. 7A. As shown in FIG. 7A, by day 18, the clinical score started to improve and by day 30 the animal was able to show improvements in locomotor motion and was able to walk. By day 40 animals demonstrated very low clinical score. Further, there was a significant weight gain over time in the treated animals as compared to control animals.

Figure 7B:
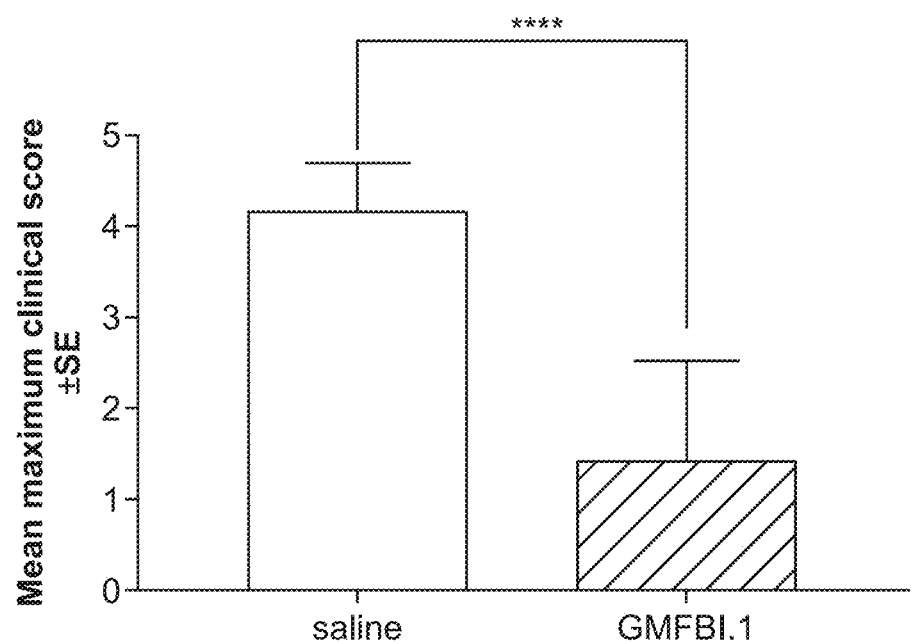
FIG. 7B shows the mean maximum clinical scores for GMFBI.1 compound treated and control animal groups.
Figure 7C:
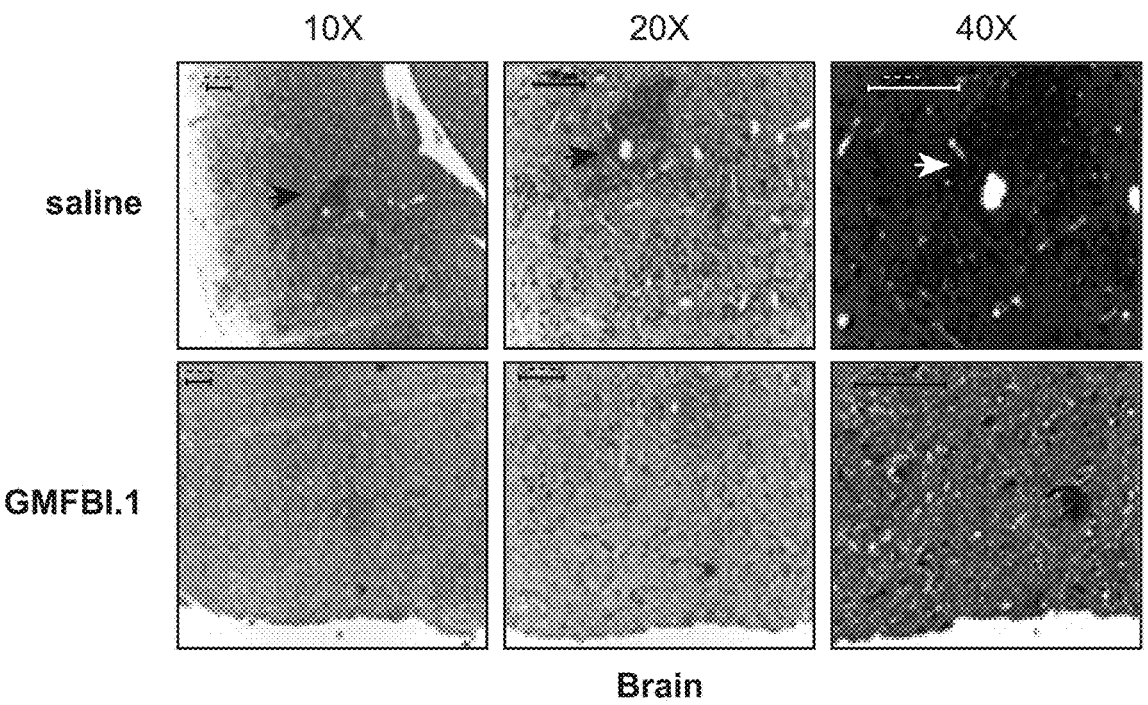
FIG. 7C shows the levels of leukocyte infiltrates in brain.
Figure 7D:
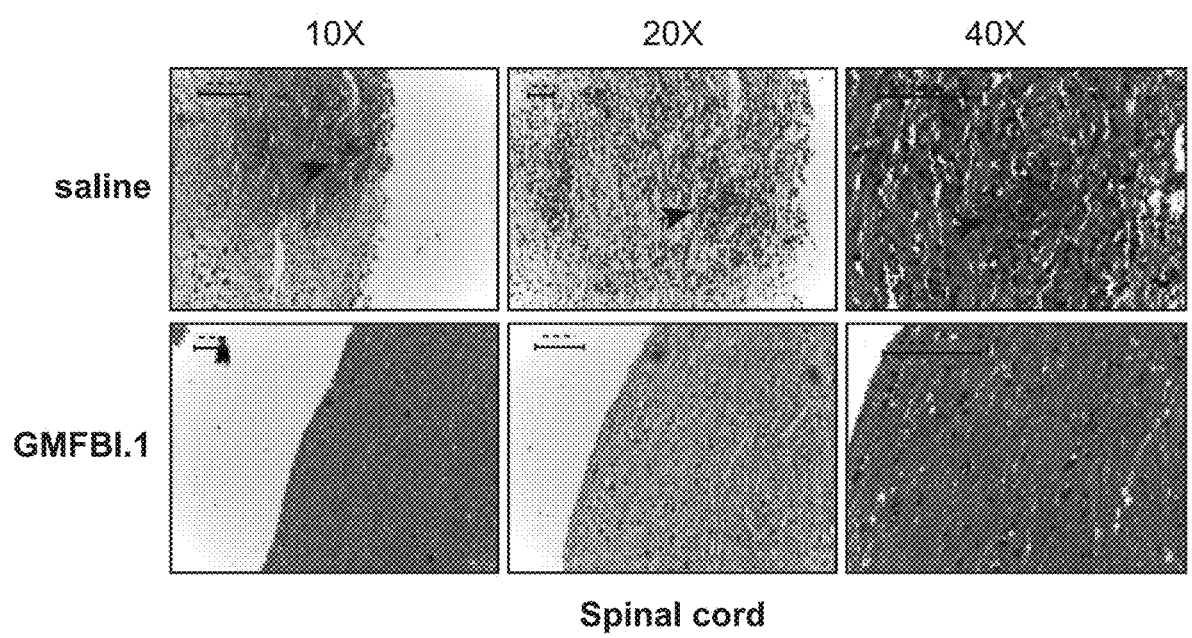
FIG. 7D shows the levels of leukocyte infiltrates in spinal cord.
Figure 7E:
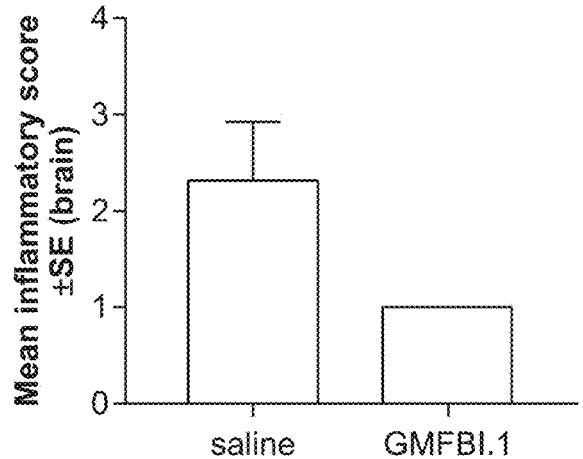
FIG. 7E shows the mean inflammation score of leukocyte infiltrates in brain.
Figure 7F:
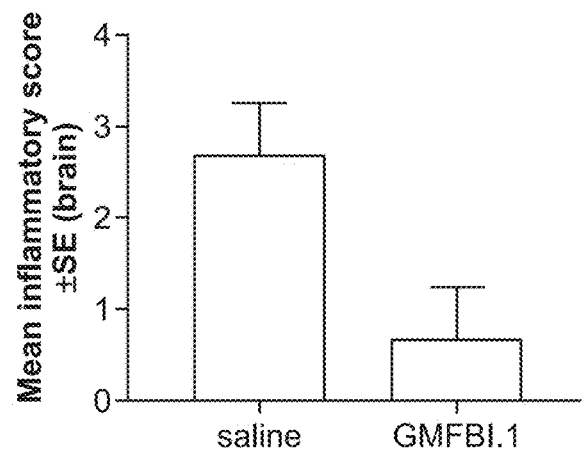
FIG. 7F shows mean inflammation score of leukocyte infiltrates in spinal cord.

Mean maximum score for GMFBI.1 compound treated and control animal groups is shown in FIG. 7B. Significant reduction in the clinical score was observed in GMFBI.1 compound treated group in comparison with the control from day 7th day after treatment ***P<0.001. Animals were sacrificed 25 days after GMFBI.1 compound treatment and the levels of leukocyte infiltrates in brain as shown in FIG. 7C and spinal cord as shown in FIG. 7D were compared against EAE control by Haematoxylin and Eosin(H and E) staining. The mean inflammation score of leukocyte infiltrates in brain and spinal cord respectively (n=3 per group) are demonstrated in FIG. 7E and FIG. 7F. In support of these experimental observations, it was observed that there is significant reduction in the number of cellular infiltrates in brain and spinal cord for GMFBI.1 compound treated animals against saline treated EAE controls (*P<0.05).

Figure 7G:
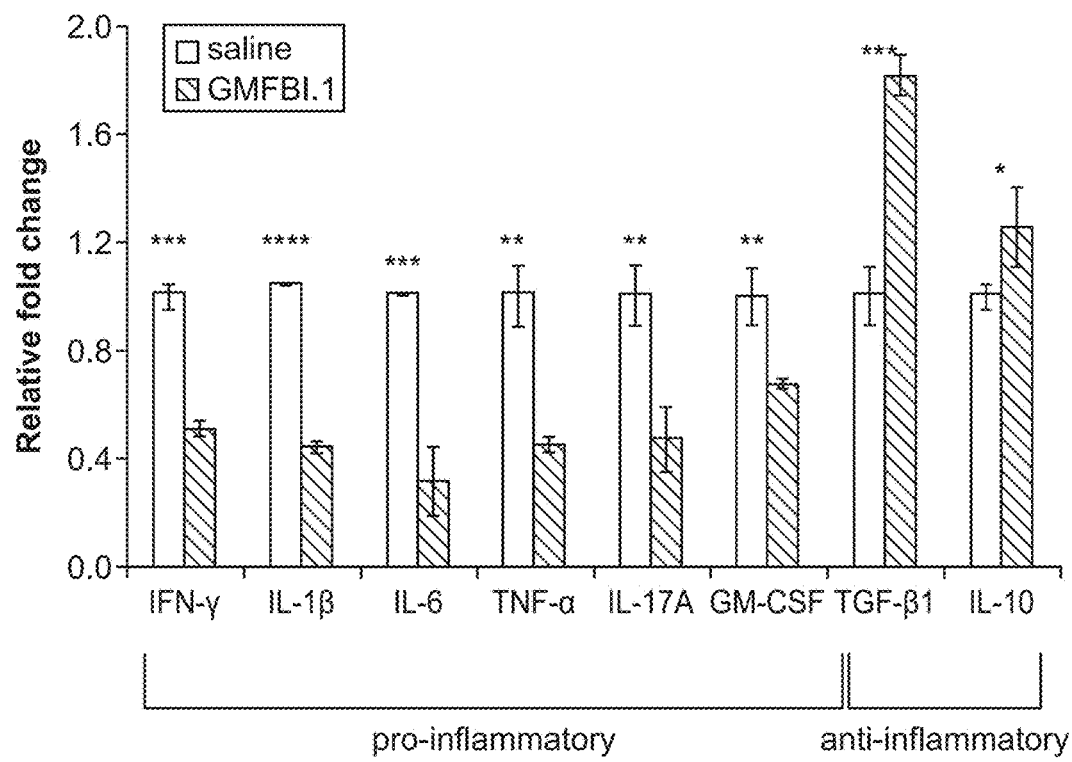
FIG. 7G show the relative fold change representation of various cytokines.

In conjunction with the reduction in clinical score, significant decrease in the proinflammatory cytokines such as IFN-γ, IL-10, IL-6, TNF-α, IL-17A and GMCSF compared to EAE controls was observed in FIG. 7G and represented as relative fold change ±SE. It was also observed that the levels of anti-inflammatory cytokines TGF-β and IL-10 were elevated significantly in GMFBI.1 compound treated animals compared to untreated EAE controls and also decrease in the levels of proinflammatory cytokines (Th1/Th17 subsets) (n=3 per group)(*P<0.05,P<0.01, *P<0.001, ****P<0.001 (G). In several diseases such as MS, such cytokines play a pivotal role in disease progression and severity during active phase of the disease. Significant down regulation of IL-6 and IL-17A by GMFBI.1 could alter the pathogenesis brought about by the Th1/Th17 paradigm in the course of the MS disease. GMFBI.1 down regulated significantly the levels of IL1-β, IFN-γ, TNF-α and IL-6 following treatment which may be involved in the pathogenesis such as by activation of macrophases, increase ROS production and drive the homing of T cells into CNS.

From FIG. 7G, it is observed that down regulation of these inflammatory cytokines has potential significance in the therapy and increased levels of anti-inflammatory cytokines particularly IL-10 and TGF beta levels. In MS patients, the levels of TGF beta and IL-10 are low compared to healthy individuals and significant down regulation of IL-17 are promising as IL-17 drives the inflammation in EAE and MS disease.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the system and method of the present invention disclosed herein without departing from the spirit and scope of the invention as described here. While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

What is claimed is:

1. A method of treating multiple sclerosis by inhibiting GMF-β phosphorylation, comprising administering a therapeutically effective amount of a compound of Formula (I):

or a pharmaceutically acceptable salt thereof, wherein the inhibiting of GMF-β phosphorylation is for treatment of multiple sclerosis and wherein the compound of Formula (I) binds to the active site of Glia Maturation Factor Beta (GMF-β) protein and blocks the Ser83 phosphorylation with a binding efficiency in the range of −6.5 to −5.5 kcal/mol.

2. The method of claim 1, wherein the compound is administered at a daily dose of 0.1 to 100 mg/kg.

3. The method of claim 1, wherein the compound is administered by a route selected from oral, rectal, nasal, topical, vaginal, parenteral, subcutaneous, intramuscular, intravenous, and intradermal.

4. The method of claim 1, wherein the compound interacts with Arg24, Thr27, Ser72, Arg81, Val82, and Ser83 of GMF-β leading to high affinity interaction and inhibits phosphorylation of Ser83 of GMF-β.

* * * * *